(12) United States Patent
Umapathy et al.

(10) Patent No.: US 10,024,799 B2
(45) Date of Patent: Jul. 17, 2018

(54) CHEMICAL SIGNATURE RESOLVED DETECTION OF CONCEALED OBJECTS

(71) Applicant: INDIAN INSTITUTE OF SCIENCE, Bangalore (IN)

(72) Inventors: Siva Umapathy, Bangalore (IN); Sanchita Sil, Bangalore (IN); Gagan Dhal, Bangalore (IN); Freek Ariese, Bangalore (IN)

(73) Assignee: INDIAN INSTITUTE OF SCIENCE, Bangalore (IN)

( * ) Notice: Subject to any disclaimer, the term of this patent is extended or adjusted under 35 U.S.C. 154(b) by 0 days.

(21) Appl. No.: 15/122,170

(22) PCT Filed: Feb. 13, 2015

(86) PCT No.: PCT/IN2015/000083
§ 371 (c)(1),
(2) Date: Aug. 28, 2016

(87) PCT Pub. No.: WO2016/103272
PCT Pub. Date: Jun. 30, 2016

(65) Prior Publication Data
US 2016/0370298 A1    Dec. 22, 2016

(30) Foreign Application Priority Data

Dec. 27, 2014   (IN) .................................. 6626/2014

(51) Int. Cl.
*G01J 3/44*     (2006.01)
*G01N 21/65*   (2006.01)
(Continued)

(52) U.S. Cl.
CPC ............. *G01N 21/65* (2013.01); *G01B 11/00* (2013.01); *G01J 3/0221* (2013.01); *G01J 3/44* (2013.01);
(Continued)

(58) Field of Classification Search
CPC . G01B 11/00; G01J 3/0221; G01J 3/44; G01J 3/4412; G01N 21/65;
(Continued)

(56) References Cited

U.S. PATENT DOCUMENTS

2010/0038550 A1\* 2/2010 DeVito ................ G01V 5/0069
250/370.11
2011/0220793 A1\* 9/2011 Thomas .................. H01J 37/20
250/307

(Continued)

*Primary Examiner* — Sunghee Y Gray
(74) *Attorney, Agent, or Firm* — Mark M. Friedman

(57) ABSTRACT

The invention provides a method for chemical signature resolved detection of a concealed object within a system. The method includes irradiating the system at a plurality of positions with aplurality of electromagnetic radiation of specific wavelength; capturing a certain component of the scattered electromagnetic radiation from the object at a plurality of locations along various 3D planes around the system; obtaining a plurality of profiles from the captured component of the scattered electromagnetic radiation; filtering the profiles to obtain a chemical signature specific to the object; and resolving the chemical signatures to detect the concealed object, wherein the step of detection includes determination of the shape, size and location of the object.

9 Claims, 7 Drawing Sheets

(51) Int. Cl.
*G01B 11/00* (2006.01)
*G01J 3/02* (2006.01)

(52) U.S. Cl.
CPC .... *G01J 3/4412* (2013.01); *G01N 2201/0221* (2013.01); *G01N 2201/06113* (2013.01); *G01N 2201/0826* (2013.01); *G01N 2201/0833* (2013.01)

(58) Field of Classification Search
CPC . G01N 2201/0221; G01N 2201/06113; G01N 2201/0826; G01N 2201/0833
USPC .......................................... 356/301; 250/338.4
See application file for complete search history.

(56) References Cited

U.S. PATENT DOCUMENTS

| | | | |
|---|---|---|---|
| 2013/0135609 A1* | 5/2013 | Gardner, Jr. .............. | G01J 3/44 356/51 |
| 2014/0226157 A1* | 8/2014 | Dogariu ................... | G01J 3/44 356/301 |
| 2014/0252234 A1* | 9/2014 | Lee ........................ | G01N 21/65 250/341.1 |

* cited by examiner

CHEMICAL SIGNATURE RESOLVED DETECTION OF CONCEALED OBJECTS

FIELD OF INVENTION

The invention generally relates to the field of physical chemistry and particularly to a method and a system for chemical signature resolved detection of concealed objects using multiple excitation Raman spectroscopy.

BACKGROUND

Biomedical imaging techniques such as X-ray imaging, MRI, fluorescence and optical coherence tomography, NIR absorption imaging, etc., providing global morphological/density/absorption changes of the hidden components are based on retrieving information from the photons that have travelled inside the sample of interest. These techniques, in general, provide information on morphology or density, either based on the response of labels (e.g. dyes, fluorophores), or changes in the bulk properties of the materials but with no specific information on the chemical composition of the samples.

Photons in a multiple scattering media contain both Rayleigh and Rarnan scattered photons, recording Rarnan scattered light yields the structure and chemical nature of the molecules. In general, Raman spectroscopic observations are made at fixed collection angles, such as, 90°, 135°, 180° and transmission techniques. The problem with the geometry specific collection is that, it restricts the observations of Raman signals either from or near the surface of the materials. However, Raman signals of objects are generally scattered in all 360° angles or planes and therefore these signals, in principle, can be retrieved irrespective of the illumination or collection geometry. Signals can be obtained from all the observable angles from all the sides.

Since the multiply scattered light contains both Rayleigh and Raman scattered photons, recording Raman scattered light has been explored for identifying the structure and chemical nature of the molecules. Examples of known techniques that record Raman scattering include but are not limited to spatially offset Raman spectroscopy (SORS) and transmission Raman spectroscopy (TRS). SORS works on the principle of backscattering collection geometry wherein the scattering from the surface along with the Raman signal of the sample located deeper in the sample, contribute to the scattering. U.S. Pat. No. 7,911,604, assigned to The Science and Technology Facilities Council, discloses a method and an apparatus for screening objects using Raman scattering methods to detect the presence of predefined substances or classes of substances. The predefined substances may be hazardous, toxic, or explosive. Radiation is supplied to an incident region of an object. Scattered light is collected from a collection region on the surface of the object spaced from the incident region. The characteristics of the scattered light include Raman features related to the surface and predefined substances. The Raman features allow the presence, or not, of the predefined substances to be determined. One of the primary disadvantages of SORS is that the detection is restricted to a specific experimental geometry, which involves strict description of finite distance between light input and collection of scattered light. For example, SORS works only in the backscattering geometry with fixed orientation of incident and collection being either in the same axis or plane with varying distance between incident and collection locations.

Transmission Raman spectroscopy (TRS) is another technique adopted for screening objects. Raman signals are obtained from the transmission side of the sample. TRS cannot distinguish the individual layers of different chemicals in a multi-component layered system. U.S. Pat. No. 8,054,463, assigned to The Regents of the University of Michigan, discloses a method and a system for measuring sub-surface composition of a sample. An illumination area of a sample is irradiated using a light source and the light scattered from a plurality of emitting surface areas of the sample is received. Each emitting surface area of the sample is at a different location. For each emitting surface area, spectral content information associated with received light corresponding to that emitting surface area is determined, and composition information corresponding to a sub-surface region of the sample is determined based on the determined spectral content information. The Regents' Patent is restricted to backscattering and transmission geometry. The illumination and collection geometries are located in the same plane. The maximum offset allowed, between the illumination and collection geometry is 90°. Further, the collection geometry is restricted to only 2D plane. Hence, the image obtained is predominantly a 2D image which is then reconstructed to obtain a 3D image. The depth of detection is only up to 22 mm.

The current 3D imaging techniques are based upon observing the changes of the optical properties of tissues/materials based on absorption values or density differences. However, chemical specific information cannot be retrieved using such methods. Raman spectroscopy can readily yield molecular specific information. However, in order to obtain a complete shape of an object concealed within another layer, it is pertinent to acquire signals globally, i.e. from all the sides, planes and angles. Hence, there is a need for a method that can not only identify concealed samples but also profile them based on their shapes at various levels of depth.

BRIEF DESCRIPTION OF DRAWINGS

So that the manner in which the recited features of the invention can be understood in detail, some of the embodiments are illustrated in the appended drawings. It is to be noted, however, that the appended drawings illustrate only typical embodiments of this invention and are therefore not to be considered limiting of its scope, for the invention may admit to other equally effective embodiments.

SUMMARY OF THE INVENTION

One aspect of the invention provides a method for chemical signature resolved detection of a concealed object within a system. The method includes irradiating the system at a plurality of positions with a plurality of electromagnetic radiation of specific wavelength; capturing a certain component of the scattered electromagnetic radiation from the object at a plurality of locations along various 3D planes around the system; obtaining a plurality of profiles from the captured components of the scattered electromagnetic; radiation; filtering the profiles to obtain a chemical signature specific to the object; and resolving the chemical signatures to detect the concealed object, wherein, the step of detection includes determination of the shape, size and location of the object.

Another aspect of the invention provides an apparatus for chemical signature resolved detection of concealed objects in a system.

DETAILED DESCRIPTION OF THE INVENTION

Various embodiments of the invention provide a method and a system for chemical signature resolved detection of concealed objects in a multiple scattering media. The method works on the principle of acquisition of Raman signal from multiple angles through multiple scattering of light in a randomly distributed medium. The multiply scattered Raman signal obtained at various angles and various planes enables the method to probe both strongly and weakly scattering media located at a depth within overlying multiple scattering systems. Each particle in a sample is excited by the external electromagnetic field and the resultant field scattered by all other particles. The field scattered by the particle depends on the total field to which it is exposed. The light scattered at other positions in the medium contribute to the irradiance at a position of observation. Therefore, the scattered light merely changes direction and is lost from a beam propagating in a particular direction, but contributes to other directions. The total irradiance scattered by the collection in any direction is the sum of the irradiances scattered by the individual particles in that direction. The total signal observed at any point of observation is dependent on the scattering cross section, the number density of particles and the medium thickness. Therefore, the Raman signal obtained from multiple angles enables probing of dense media of thickness exceeding a few tens of mm and detecting samples buried deep inside them. Since Raman signals obtained are specific to the scatterer, accurate profiling of substances, to obtain specific chemical signatures, is possible irrespective of the extent to which the source is scattered. In addition to the depth specific chemical signature of the object within the multiple scattering medium, by scanning the entire length of the system, one can retrieve information about the shape of the system under study.

Figure 1A:
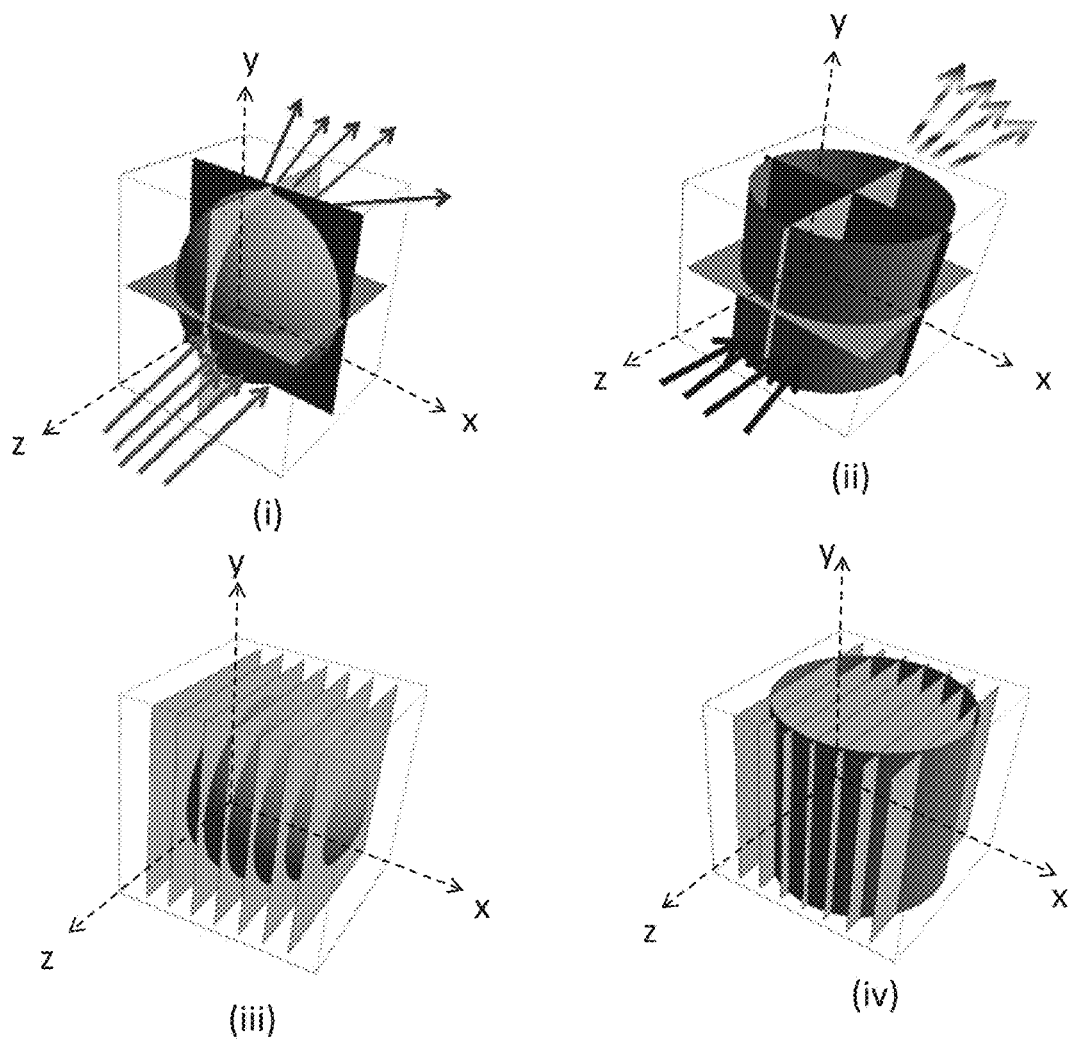
FIG. 1a shows the principles of illumination of a sample and collection of the multiply scattered radiation, according to an embodiment of the invention.
Figure 1B:
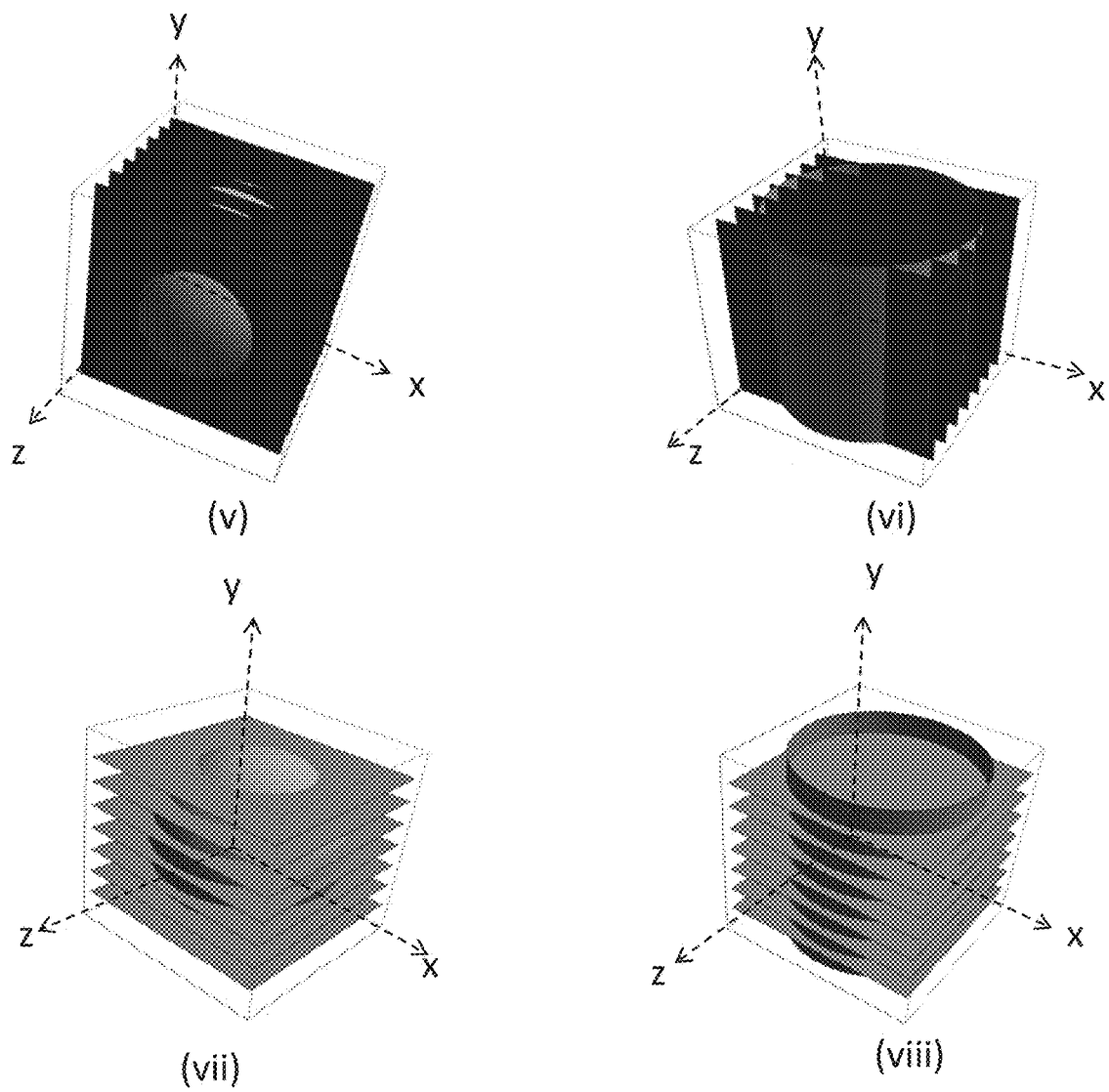
FIG. 1b shows the principles of collection of the multiply scattered radiation from a sample, according to another embodiment of the invention.
Figure 2:
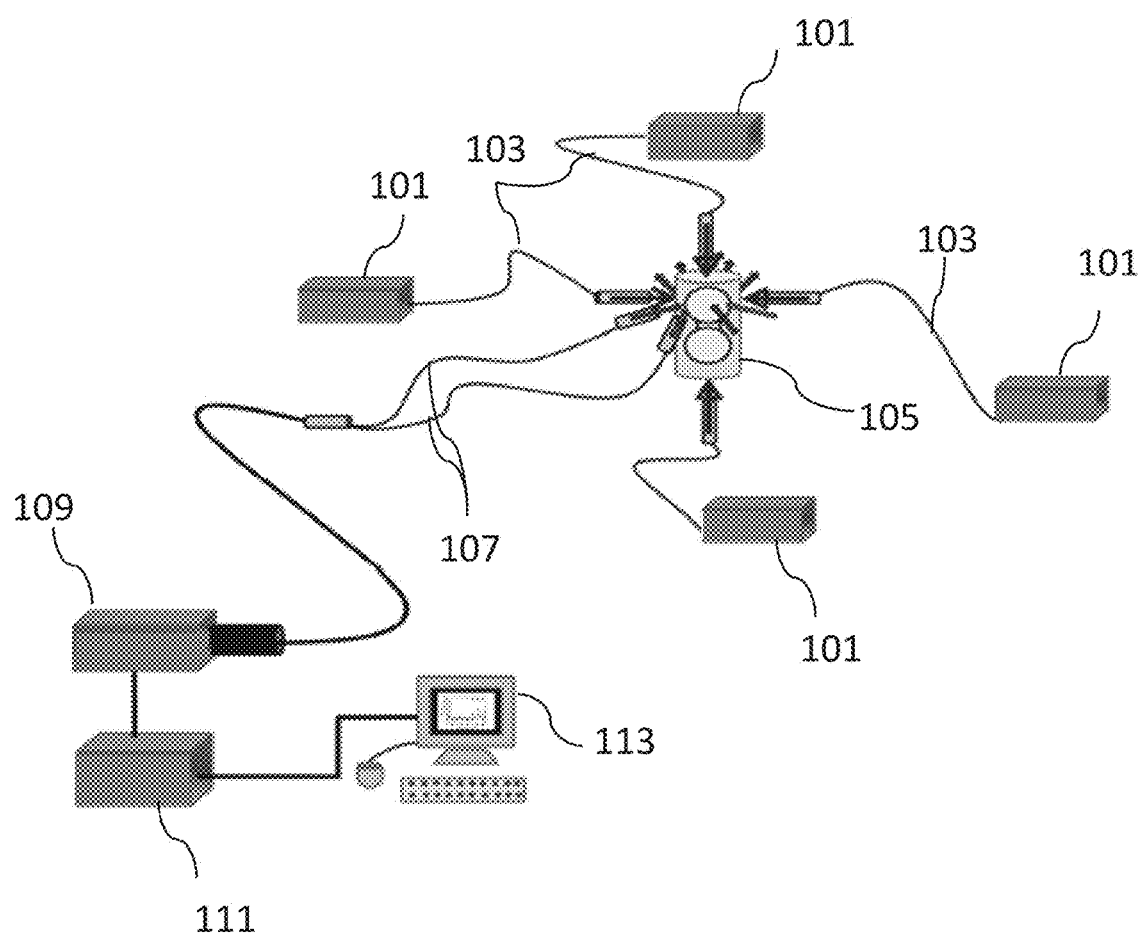
FIG. 2 shows an experimental setup for chemical signature resolved detection of concealed objects, according to an embodiment of the invention.

The multiple scattering Raman light is not restricted to a particular geometry such as back scattering and transmission. Hence collection over $4\pi$ angles and $4\pi$ planes enables global information including shape, size and location from the sample under observation. Additionally, collection of the data over $4\pi$ angles and $4\pi$ planes improves the signal to noise ratio. FIG. 1a and 1b illustrate the principles of illumination of a sample and collection of the multiply scattered radiation, according to an embodiment of the invention. For instance, if an excitation is provided at the bottom end of the x-plane in a sphere or a cylinder, as shown in FIG. 1a(i) and FIG. 1a(ii), one can, in principle, observe the signals, at the top-end to bottom-end of the y and z planes, in addition to measuring signals on the top-end of the x-plane as illustrated in FIGS. 1a(iii), 1a(iv), 1b(v), 1b(vi), 1b(vii) and 1b(viii). FIG. 2 illustrates an experimental setup for chemical signature resolved detection of concealed objects, according to an embodiment of the invention. The figure shows an arrangement for multiple excitations and multiple angle shape selective detection of an object in a multilayered sample, according to an embodiment of the invention. The example of the object includes but is not limited to chemical contaminants, tissue contaminants, modified tissues, degenerated tissues and tumours. In one embodiment of the invention, the object is 1,4-dicyanobenzene (DCB) in a dumbbell shape. The example of multiple scattering media include but is not limited to turbid media, tissues, and all such non-homogeneous media exhibiting multiple scattering. In one embodiment of the invention, the multiple scattering medium is ammonium nitrate. In another embodiment of the invention, the multiple scattering medium is chicken tissue. In one embodiment of the invention, laser beam from a source/s 101 is delivered through optical fibers 103. The laser beams are incident on a non-homogenous sample containing a concealed complex shape 105. In one example of the invention, four optical fibers (core diameter 400 µm) are used to irradiate the sample 105 at different location. The scattered light containing the inelastic (Raman) scattered photons emerge out of the sample 105 at multiple directions due to multiple continuous scattering. These photons are collected using a plurality of collection fibers 107 attached to the sample 105 at varying angles with respect to the incident beam. In one example of the invention, nine collection fibers with the same core diameter are placed around the sample at known angles. The collection fibers 107 are bundled and placed in front of a collection optics arrangement fixed to the entrance slit of a spectrometer 109. The spectrometer 109 is connected to a detector 111. The output of the detector 111 is sent to an analysis unit 113.

In one embodiment of the invention, the electromagnetic radiation is a monochromatic coherent source of light. The wavelength of the source of light for excitation is in the range of 500 nm to 1400 nm. The spectral range is dependent on the spectrometer and the detector while the penetration depth depends upon the selection of the source wavelength. In one example of the invention, the wavelength of the source of light for excitation is chosen in the IR region. In a preferred embodiment of the invention, an 830 nm laser is used as a source of light for excitation for investigating strongly scattering media in order to avoid fluorescence and absorption, and to attain a better penetration depth.

The apparatus as described herein is used for detecting specific chemical signatures and shapes of the scattering samples concealed in multilayered sample. The chemical signatures are identified independent of the collection geometry. The collection geometry as referred herein means orientation and position of the collection arrangement. The collection arrangement includes but is not limited to lenses, fiber optics and all such devices capable of capturing the scattered electromagnetic radiation, as obvious to a person skilled in the art.

Figure 3A:
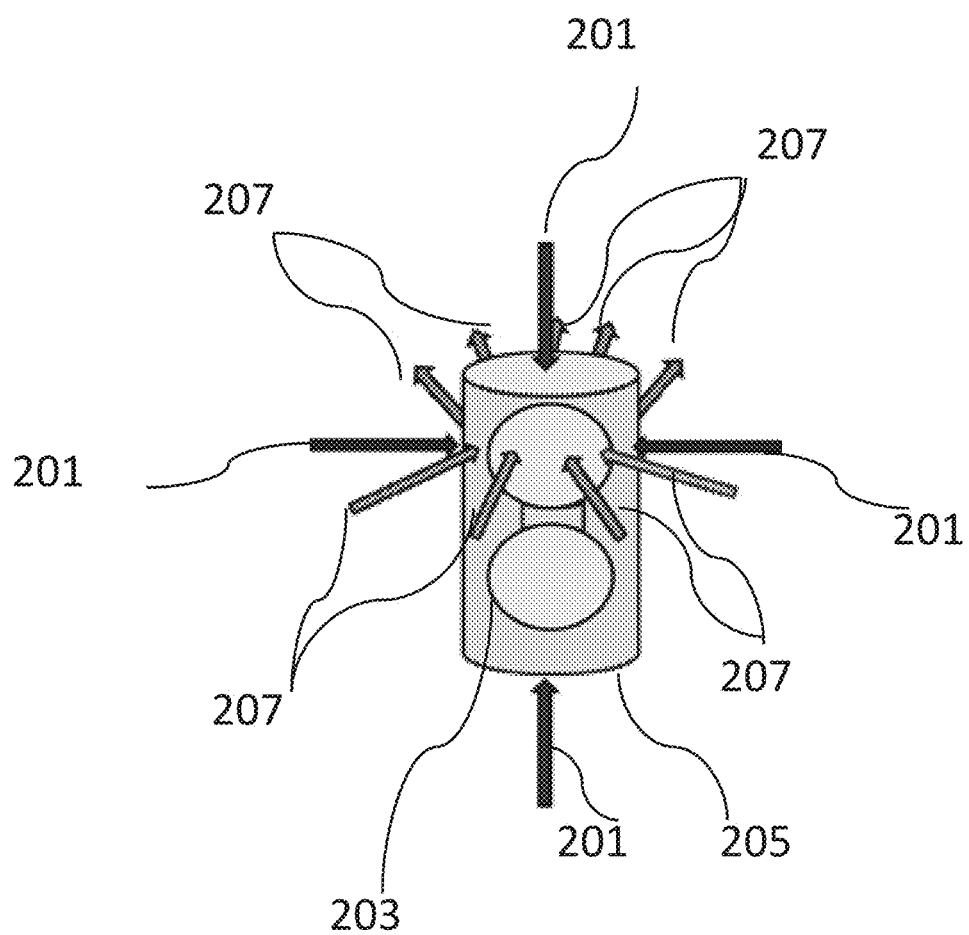
FIG. 3a shows arrangement of illumination fibers and collection fibers for chemical signature resolved detection of concealed objects, according to an embodiment of the invention.

FIG. 3a shows arrangement of the illumination fibers and the collection fibers for chemical signature resolved detection of concealed objects, according to an embodiment of the invention. In one embodiment of the invention, four illumination fibers 201 are used to irradiate a sample 203 concealed inside a container 205 at different locations. The core diameter of the illumination fibers 201 is approximately 400 μm. For collection of scattered light nine collection fibers 207 are arranged outside the sample 203 at known angles. The core diameter of the collection fibers 207 is approximately 400 μm. Signals are collected from the top position of the container 205 and the collection fibers 207 are moved down after each collection by 100 μm.

Figure 3B:
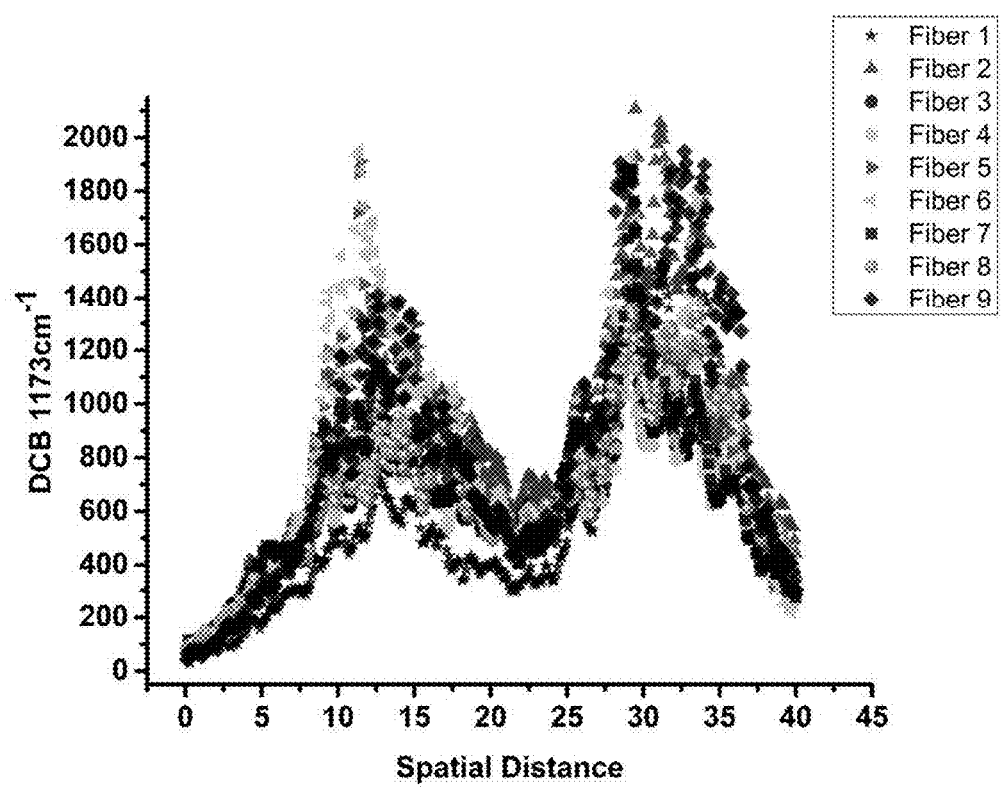
FIG. 3b shows intensity variation of 1,4-dicyanobenzene (DOB) throughout the length of the beaker, according to an embodiment of the invention.

FIG. 3b shows intensity variation of the sample (1,4-dicyanobenzene) throughout the length of the container. Hence, a plurality of images are obtained from the entire length of the container. In one embodiment of the invention, about 400 images are obtained from the entire length of the sample.

Figure 3C:
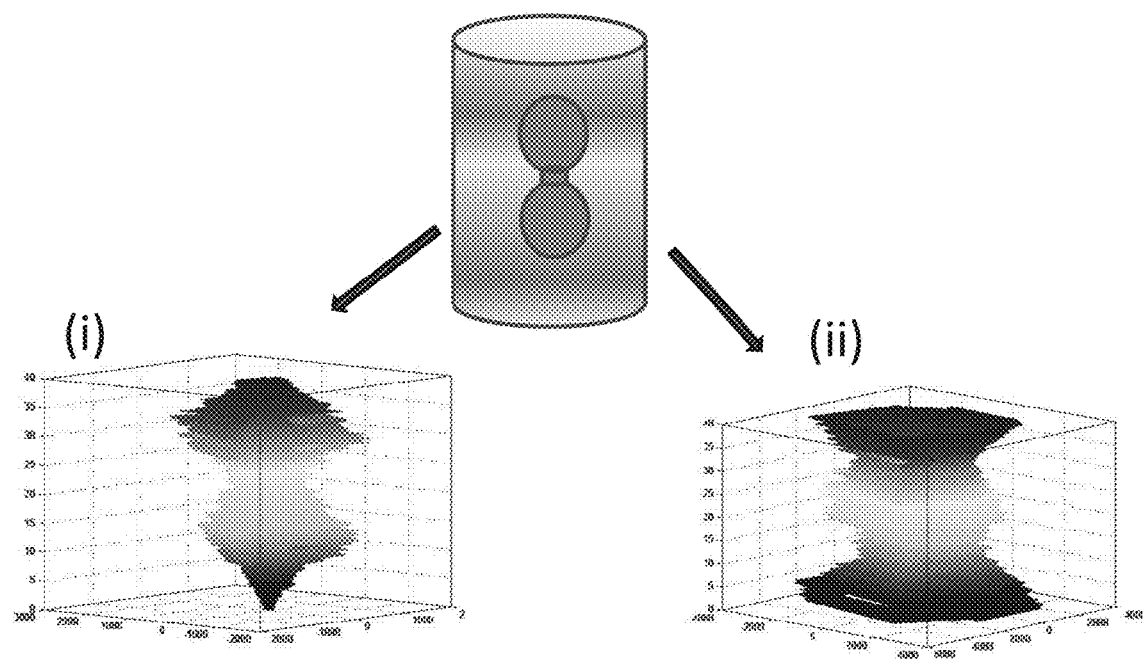
FIG. 3c shows the 3D images reconstructed for (i) the inner object (1,4-dicyanobenzene) and (ii) the outer material (ammonium nitrate) using multiple excitation and multiple collection, according to an embodiment of the invention.

After obtaining the 2D images, 3D image reconstruction of the shape of the original object, 1,4-dicyanobenzene (DCB), concealed inside ammonium nitrate is performed. FIG. 3c shows the 3D images reconstructed for (i) the inner object (1,4-dicyanobenzene) and (ii) the outer material (ammonium nitrate) using multiple excitation and multiple collection, according to an embodiment of the invention.

The 2D image files are imported to MATLAB 2009 . The row pixels from the image plot for each fiber i.e. pixel 10-19 for fiber 1, 20-29 for fiber 2 and so on are selected. For instance, image of the fiber 1 is obtained from $10^{th}$ row pixel to the $19^{th}$ row pixel. The spectra of the individual row pixels are then plotted followed by processing the spectra. The ten row pixels are averaged to obtain the spectra for an individual fiber at a given vertical location. Then the spectra are baseline subtracted, smoothened using a MATLAB code. After the processing step, the spectra are re-plotted from the processed image files of the individual pixels for each fiber. The area under the curve for the frequencies of interest is obtained. This process is iterated for all the fibers at each location. This means that around 36000 spectra are considered for this particular demonstration (9 fibers×10 rows (COD)×400 spatial points). The area under the curve obtained for the individual frequencies (1173 $cm^{-1}$ for 1,4-dicyanobenzene (DCB) and 1040 $cm^{-1}$ for ammonium nitrate) yields the total intensity (r) of the peaks at a particular angle, i.e. fiber position (θ) and location (h). Therefore, a set of values in the form of a cylindrical coordinate (r, θ, h) system is obtained. Where r is the intensity of the 1,4-dicyanobenzene (DOB) and ammonium nitrate bands, θ corresponds to the angle at which the individual fibers are placed ($f_1$=33°, $f_2$=65 and so on) and h corresponds to the height or the vertical spatial position ($h_1$, $h_2$, . . . , $h_{40}$). The final reconstructed shape is obtained by using another MATLAB code to transform the cylindrical coordinate to the Cartesian coordinate.

Figure 4:
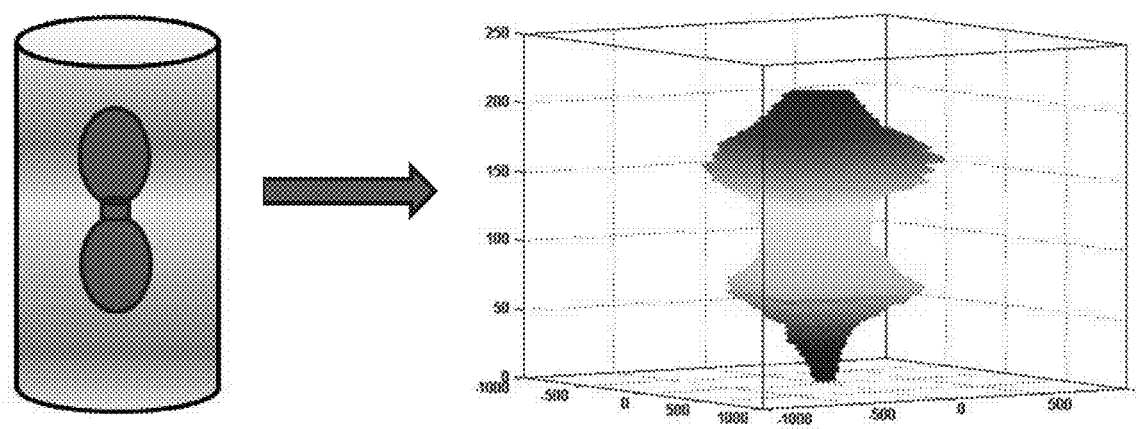
FIG. 4 shows the 3D images reconstructed for specific detection of 1,4-dicyanobenzene (DCB) in the shape of a dumbbell concealed inside a chicken tissue of 40 mm using multiple excitation, according to an embodiment of the invention.

In an alternate embodiment, 1,4-dicyanobenzene in the shape of a dumbbell is concealed inside a chicken tissue of 40 mm thickness. From 2D images, 3D images are reconstructed. FIG. 4 shows the 3D images reconstructed for specific detection of 1,4-dicyanobenzene in the shape of a dumbbell concealed inside a chicken tissue of 40 mm using multiple excitation, according to an embodiment of the invention.

The invention described herein provides a method and an apparatus for obtaining 3D shapes of complex materials concealed within a multiple scattering sample e.g. tissue. The method predominantly utilizes a Raman spectroscopic technique that employs multiple excitations and is geometry independent. The spectroscopic technique is capable of probing any type of scattering samples and identifies individual layers in a multilayer system. In addition, 3D shapes are reconstructed using the 2D spectral image scans. One of the primary advantages of the method and the apparatus described herein is that the method is independent of the experimental geometry. Scan along each position generates spectral information of a plane containing the multilayered materials. A complete image reconstruction adds up all the scans to yield the 3D image. The multiple excitations ensure distribution of photons throughout the scattering medium. The multiple angle collection over 4π angles and 4π planes ensures collection of Raman signals from all sides and at all angles. The technique basically depends on recording Raman signals from all observable angles, planes and sides of the sample, coming out in all directions. Further, the technique as described herein is a portable device which can be a potential diagnostic tool for non-invasive detection, screening and 3D imaging of bone anomalies, calcification and breast scanning for tumors.

The foregoing description of the invention has been given merely to illustrate the invention and is not intended to be limiting. Since modifications of the disclosed embodiments incorporating the spirit and substance of the invention may occur to a person skilled in the art, the invention should be construed to include everything within the scope of the appended claims and equivalents thereof.

We claim:

1. A method for chemical signature resolved detection of a concealed object within a system, the method comprising:
   a. irradiating the system with a plurality of electromagnetic radiation of a specific wavelength around the object;
   b. capturing a Raman scattered radiation from the object at 4π angles and/or 4π planes around the system, wherein the Raman scattered radiation is captured in steps of at least 0.1 degree with reference to an initial position of capture around the object;
   c. obtaining a plurality of profiles from the captured component of the scattered electromagnetic radiation;
   d. filtering the profiles to obtain a chemical signature specific to the object; and
   e. resolving the chemical signatures to detect the concealed object;
   wherein, the step of detection includes determination of the shape, size and location of the object.

2. The method according to claim 1, wherein the wavelength of the electromagnetic radiation is in the range of 500 nm to 1400 nm.

3. The method according to claim 1, wherein the component of the scattered electromagnetic radiation is Raman scattering.

4. The method according to claim 1, wherein the capturing of the scattered electromagnetic radiation is independent of the collection geometry.

5. The method according to claim 1, wherein the captured electromagnetic radiation is an amplified scattering obtained through multiple scattering of the incident electromagnetic radiation from the object.

6. The method according to claim 1, wherein the multiple scattering is achieved by targeting the incident electromagnetic radiation on the object with at least one of a plurality of orientations, angles, positions or a combination thereof.

7. The method according to claim 1, wherein the object is selected from a list comprising of chemical contaminants, tissue contaminants, modified tissues, degenerated tissues, tumors and objects capable of providing a chemical signature.

8. The method according to claim 1, wherein the system can be a translucent system or an opaque system.

9. The method according to claim 1, wherein the system is selected from a list comprising of powdered materials, containers made of plastic, metal or fabric, processed meat and biological organisms.

* * * * *